United States Patent [19]

Linnau et al.

[11] Patent Number: 4,522,751
[45] Date of Patent: Jun. 11, 1985

[54] METHOD FOR PRODUCING A PREPARATION CONTAINING FACTOR VIII (AHF)

[75] Inventors: Yendra Linnau; Otto Schwarz, both of Vienna, Austria

[73] Assignee: Immuno Aktiengesellschaft für Chemisch-Medizinische Produkte, Vienna, Austria

[21] Appl. No.: 611,638

[22] Filed: May 18, 1984

[30] Foreign Application Priority Data

May 20, 1983 [AT] Austria ................................. 1858/83

[51] Int. Cl.³ .......................... C07G 7/00; A61K 35/14
[52] U.S. Cl. .................................. 260/112 B; 260/121; 424/101
[58] Field of Search .............................. 260/112 B, 121; 424/101, 177

[56] References Cited

U.S. PATENT DOCUMENTS

| | | | |
|---|---|---|---|
| 3,842,061 | 10/1974 | Andersson et al. | 424/101 X |
| 3,973,002 | 8/1976 | Hagan et al. | 260/112 B X |
| 4,022,758 | 5/1977 | Andersson et al. | 260/112 B |
| 4,069,216 | 1/1978 | Shanbrom | 260/112 B |
| 4,104,266 | 8/1978 | Wickerhauser | 260/112 B |
| 4,170,639 | 10/1979 | Liu et al. | 424/101 |
| 4,203,891 | 5/1980 | Rock | 260/112 B |
| 4,361,509 | 11/1982 | Zimmerman et al. | 260/112 B |
| 4,388,232 | 6/1983 | Eibl et al. | 260/112 B |
| 4,395,396 | 7/1983 | Eibl et al. | 424/101 |

FOREIGN PATENT DOCUMENTS 1551928 9/1979 United Kingdom .

OTHER PUBLICATIONS

New England Journal of Medicine 273, 1443–1447, 1965, Pool et al.
Johnson et al., Proc. 11th Cong. Int. Soc. Blood Transf., 1966, p. 1109.
Journal of Biol. Chemistry, vol. 177 (1949), pp. 751–766 (Gornall et al.).
A Laboratory Manual of Blood Coagulation, Blackwell Scientific Publications (1975), pp. 50–52, Austen et al.
Protides of Biological Fluids, Proceedings of 11th Colloquium (1964), pp. 370–373, Mancini et al.
Electrophoresis Manual (1977), Gebott et al., Cover, Contents, Forward Pages.

*Primary Examiner*—Howard E. Schain
*Attorney, Agent, or Firm*—Burns, Doane, Swecker & Mathis

[57] ABSTRACT

There is described a method for producing a preparation having a high content of Factor VIII (AHF), i.e. with a specific activity of at least 1.5 units of Factor VIII/mg protein, immunoglobulin G (IgG) of from 15 to 30 mg/1000 units of Factor VIII and fibrinogen of from 20 to 40 mg/100 units of Factor VIII. The method consists in that a Factor VIII containing plasma fraction is dissolved in a buffer, the solution is purified from undesired proteins by precipitation and is concentrated, the precipitation of undesired proteins being carried out in the presence of sulfated polysaccharide at a pH of from 6 to 7. After separation of the undesired proteins, a Factor VIII concentrate is precipitated, dissolved and processed into stable form. If desired, an antithrombin III-heparin complex or an antithrombin III-heparinoid complex is added to the solution.

10 Claims, No Drawings

METHOD FOR PRODUCING A PREPARATION CONTAINING FACTOR VIII (AHF)

The invention relates to a method for producing a Factor VIII (AHF) containing preparation.

There are already known Factor VIII (AHF) concentrates that are produced of human or animal plasma and exhibit an increased Factor VIII activity as compared to native plasma. Known methods for producing Factor VIII concentrates, as a fractionation measure, call upon a treatment of plasma with ethanol, with ether, with polyethylene glycol and/or with glycine. Also known is the cryoprecipitation of the plasma according to Pool (1965, "The New England Journal of Medicine" 273, 1443) or the cryoethanol precipitation of plasma according to Johnson (Congr. Int. Soc. Blood Transf., Sydney, Australia, Abstracts of Paper, p. 1109 (1966)).

In German Offenlegungsschrift No. 25 16 186 a method is, furthermore, described with which a cryoprecipitate obtained from blood plasma is mazerated, the mazerated product is suspended in a citrate-glucose buffer solution, centrifuged, and the thus obtained buffer extract is adjusted to a pH in the range of from 6.0 to 6.8. Under these conditions, a precipitation of undesired impurities takes place, whereupon the Factor VIII containing residue is sterilized and lyophilized. A Factor VIII product obtained according to this method only shows a slight specific activity of Factor VIII units/mg protein. Furthermore, also the portion of immunoglobulin G (IgG), based on the Factor VIII units, is undesiredly high.

Similar methods are described in Austrian Pat. No. 349,639 as well as in U.S. Pat. Nos. 4,170,639 and 4,104,266, wherein, also by departing from plasma, a cryoprecipitate is gained, is dissolved in a buffer solution in the neutral pH range with undesired proteins being separated, the supernatant is treated with aluminum hydroxide in order to separate the prothrombin complex, and then the Factor VIII containing solution is concentrated and lyophilized. Also with this method the specific activity of Factor VIII units/mg protein is undesiredly low. Thus, the specific activity when working after U.S. Pat. No. 4,104,266 amounts to only 0.5 to 0.6 units/mg protein.

Another method for preparing Factor VIII concentrates consists in treating the plasma with adsorbents, such as florigel, bentonite, ion exchanger and permeation-chromatographic methods.

The invention aims at avoiding the disadvantages and difficulties described and has as its object to provide a preparation containing Factor VIII (AHF), with a specific activity of at least 1.5 units of Factor VIII/mg protein, immunoglobulin G (IgG) of 15 to 30 mg/1,000 units of Factor VIII and fibrinogen of 20 to 40 mg/100 units of Factor VIII, by using the method of precipitating undesired proteins, in particular the principal amount of fibrinogen, at a pH in approximately the neutral range.

The invention by which this object is achieved, with a method of the initially defined kind, consists in that the precipitation of undesired proteins is carried out in the presence of a sulfated polysaccharide at a pH of from 6 to 7, whereupon, after discarding the precipitate, the Factor VIII containing supernatant is treated with a protein precipitating agent in the presence of salts at a pH of from 6 to 7, wherein a Factor VIII containing precipitate is obtained, which is dissolved, and, if desired, the end product is admixed with an antithrombin-III-heparin- or antithrombin-III-heparinoid complex.

By the method according to the invention, a preparation having a high specific activity of, for instance, 1.5 to 4.0 units of Factor VIII/mg protein and a low content of immunoglobulin of about 15 to 30 mg/1,000 units of Factor VIII is obtained. A preparation of this kind exhibits a very good solubility after lyophilization. The reconstitution time is no more than 0.5 to 4 min, the economy of the method according to the invention is very good, the yields are high.

According to a preferred embodiment, heparinoids, such as mucopolysaccharide polysulfuric acid ester, pentosan polysulfate, dextran sulfate are used as sulfated polysaccharides.

An advantageous method according to the invention is characterized by the combination of the following measures:

that a cryoprecipitate is dissolved in a citrate-heparinoid buffer, is adjusted to a pH of from 6.0 to 6.4, and the suspension is cooled to 0° to 25° C., preferably 4° to 8° C., with undesired proteins being precipitated, that, after discarding of the precipitate, the purified Factor VIII containing supernate solution is concentrated by precipitation with a protein precipitating agent, such as ethyl alcohol, at a pH of from 6.0 to 7.0, in the presence of 1.45 mol glycin at most and/or an ionic strength of 0.15 at least, that the Factor VIII containing precipitate is dissolved in a glycine-citrate-NaCl buffer solution in the presence of an antithrombin III-heparinoid- or antithrombin III-heparin complex and is processed into stable form.

A variant of this embodiment consists in that, after addition of the protein precipitating agent and the salts to the Factor VIII containing supernate solution, the obtained suspension is frozen and rethawed at a temperature of from 0° to 4° C., the supernatant being discarded and the Factor VIII containing precipitate being dissolved in the glycine-citrate-NaCl buffer solution in the presence of an antithrombin III-heparinoid- or antithrombin III-heparin complex and is processed into stable form.

Suitably, albumin is added to the final product for purposes of stabilization.

By specific Factor VIII activity of the preparation produced according to the invention, the ratio of Factor VIII activity/mg protein is meant. The Factor VIII activity is determined according to the socalled two-step method, i.e. according to D. E. G. Austen and I. L. Rhymes, "A Laboratory Manual of Blood Coagulation" Blackwell Scientific Publications, 1975. The protein concentration can be determined according to the method described in J. Biol. Chem. 177, 751 (1949) by A. G. Gornall, C. S. Bardawill and M. M. David.

A method for the determination of immunoglobulin G (IgG), which may be applied to the preparations according to the invention, is described in literature, namely in "A Single-Radial-Diffusion Method for the Immunological Quantitation of Proteins" by G. Mancini, J. P. Vaerman, A. O. Carbonara and J. F. Heremans, XI. Colloquium on Protides of the Biological Fluids (1964) 370, Elsevier, Amsterdam.

The principal of the determination method consists in the reaction between antigen (IgG) and antibody (anti-IgG). An immune diffusion tray of agarose (e.g. by Immuno-Diagnostika) contains the specific antiserum (anti-IgG).

$5 \cdot 10^{-3}$ ml each of the Factor VIII containing preparation and of the reference standard preparation (with a known IgG-content, based on the WHO standard) are applied into the wells. After at least 45 hours of reaction time at 20° to 24° C., the diameters of the circular precipitations are measured. On comparison with the defined immunoglobulin reference standard, the immunoglobulin concentration of the Factor VIII containing preparation is determined.

The determination of fibrinogen by means of cellulose acetate membrane electrophoresis also is described in the literature, i.e. by Michael D. Gebott, Beckman Microzone Electrophoresis Manual, Beckman Instruments, Inc. 1977, 015-0833630-C.

According to the instructions given there, it is proceeded in the following way: A cellulose acetate membrane is impregnated with veronal/veronal sodium buffer, pH 8.6 (Beckman B-2 buffer), and equilibrated. By means of a multiple sample applicator $12.5 \cdot 10^{-3}$ mg of the Factor VIII containing preparation are applied onto the equilibrated membrane. As a reference substance for the classification of the individual components (albumin, alpha-globulin, beta-globulin, fibrinogen and gamma-globulin) human plasma is used. To determine the migration speed of the components, human albumin is used as standard.

After all the samples, albumin and plasma have been applied onto the membrane, the electrophoretic separation is carried out in the microzone separation chamber (Beckman R-200) and with the power unit (Beckman 4264): electric voltage 250 V, current intensity 3 to 4 mA per membrane, time 20 minutes.

Thereafter, the protein bands are stained with Ponceau S, the excess staining solution being removed by means of a mixture of 1 part acidic acid and 19 parts methanol. The foil is dehydrated by pure methanol and made transparent by immersion into a mixture of 1 part acidic acid and 3 parts methanol. Subsequently, the foil is dried on a glass plate and evaluated densitometrically (Beckman densitometer R-112); it prints out the relative fibrinogen content of the total protein concentration. The absolute fibrinogen amount is obtained by multiplying the relative fibrinogen concentration with the protein concentration of the Factor VIII containing preparation.

The method according to the invention will be explained in more detail by the following examples:

EXAMPLE 1

6,660 ml fresh frozen plasma were thawed at 0° C. to +4° C. The cryoprecipitate formed was separated by centrifugation and dissolved in 700 ml trisodium citrate solution containing 0.1 mg dextran sulfate (Pharmacia) per ml and 30 units of aprotinin per ml. The pH of the solution was adjusted to 6.3 and the temperature was adjusted to 4° C. A precipitate formed, which was separated by centrifugation and discarded.

By the addition of 8% ethanol, the Factor VIII containing fraction was precipitated, the immunoglobulins (IgG, IgA, IgM), for the major part, being maintained in solution by adding amino acids, such as 10% glycine, or by increasing the ionic strength by means of NaCl or sodium citrate. The separated precipitate containing the Factor VIII containing fraction was dissolved in a glycine-citrate-NaCl buffer containing an antithrombin III-heparin complex with an antithrombin concentration of 0.05 U per ml; then, the dissolved precipitation was filled into final containers and lyophilized.

The preparation of this antithrombin III-heparin complex was carried out as follows:

To 1 l plasma 80,000 U of heparin were added, and it was stirred at +4° C. for 30 min. After stirring in 1 g DEAE-Sephadex A 50, it was stirred at +4° C. for further 2 hours. The loaded gel was separated by means of a Büchner funnel and was washed twice with 100 ml each of a phosphate and citrate buffered isotonic saline solution in order to remove undesired proteins.

The loaded, washed gel was suspended in 50 ml of the above-mentioned buffer and a conductivity of 42 mS/cm was adjusted by the addition of solid NaCl. After one hour of stirring at +4° C., it was separated by means of a Büchner funnel and the antithrombin III-heparin complex was recovered in the eluate, the eluate having been dialyzed against saline.

The data of the product obtained according to this Example—determined according to the above cited literature—are as follows:

| Factor VIII units/mg protein | 1.5 |
| IgG/1000 units Factor VIII | 17.0 mg |
| Fibrinogen content/100 units Factor VIII | 35 mg |
| Reconstitution time | 4 min |

EXAMPLE 2

The preparation was produced in the same manner as in Example 1, yet a mucopolysaccharide polysulfuric acid ester was used instead of dextran sulfate. The data of this product were as follows:

| Factor VIII units/mg protein | 3.1 |
| IgG/1000 units Factor VIII | 15.6 mg |
| Fibrinogen content/100 units Factor VIII | 30 mg |
| Reconstitution time | 1 min |

EXAMPLE 3

The preparation was produced in the same manner as in Example 1, yet a pentosan polysulfate (SP 54) was used instead of dextran sulfate and the dissolving buffer contained an antithrombin III-heparinoid complex at a concentration of 0.05 units/ml. This antithrombin III-heparinoid complex was prepared in the following manner:

To 1 l plasma 3 g polyanion SP 54 were added and stirred at +4° C. for 30 min. After stirring in 2.5 g DEAE-Sephadex A 50, it was stirred at +4° C. for further two hours. The gel was separated by means of Büchner funnels and washed twice with 200 ml of a phosphate- and citrate-buffered isotonic saline solution in order to remove undesired proteins. The washed gel was suspended in 100 ml of the above mentioned buffer and a conductivity of 60 mS/cm was adjusted by the addition of solid sodium chloride. After one hour of stirring at +4° C., it was separated by means of Büchner funnels, and the antithrombin III-heparinoid complex (SP 54) was recovered in the eluate, the eluate having been dialyzed against saline.

The data of the product prepared according to this Example were the following:

| Factor VIII units/mg protein | 2.47 |

| | |
|---|---|
| IgG/1000 units Factor VIII | 27.0 mg |
| Fibrinogen content/100 units Factor VIII | 33 mg |
| Reconstitution time | 1 min |

EXAMPLE 4

7,000 ml fresh frozen plasma were thawed at 0° to +4° C. The cryoprecipitate formed was separated and dissolved in 550 ml trisodium citrate solution containing mucopolysaccharide polysulfuric acid ester. The pH of the solution was adjusted to 6.65 and the temperature was adjusted to 1° C. A precipitate formed, which was separated and discarded. The Factor VIII containing fraction was precipitated by the addition of 8% ethanol and 7.5% glycine to the supernatant. The suspension was deep-frozen and re-thawed at 0° to +4° C.

After separation of the Factor VIII containing precipitate the latter was dissolved, filled into containers and lyophilized. The data of this product were as follows:

| | |
|---|---|
| Factor VIII units/mg protein | 1.66 |
| IgG/1000 units Factor VIII | 22.0 mg |
| Fibrinogen content/100 units Factor VIII | 40 mg |
| Reconstitution time | 3 min |

EXAMPLE 5

5,000 ml fresh frozen plasma were thawed at 0° to +4° C. The cryoprecipitate formed was separated and dissolved in 350 ml trisodium citrate solution containing pentosan polysulfate. The pH of the solution was adjusted to 6.20 and the temperature was adjusted to 8° C. A precipitate formed, which was separated and discarded. The Factor VIII containing fraction was precipitated by the addition of 15% glycine to the supernatant. The suspension was deep-frozen and re-thawed at 0° to +4° C.

After separation of the Factor VIII containing precipitate, the latter was dissolved, filled into containers and lyophilized. The data of this product were the following:

| | |
|---|---|
| Factor VIII units/mg protein | 3.80 |
| IgG/1000 units Factor VIII | 20 mg |
| Fibrinogen content/100 units Factor VIII | 21 mg |
| Reconstitution time | 2 min |

What we claim is:

1. A method of producing a preparation containing Factor VIII (AHF) from a Factor-VIII-containing plasma fraction, said preparation containing Factor VIII (AHF) having a specific activity of at least 1.5 units of Factor VIII/mg protein, immunoglobulin G (IgG) of from 15 to 30 mg/1000 units of Factor VIII and fibrinogen of from 20 to 40 mg/100 units of Factor VIII, said method comprising the steps of:

(a) dissolving said Factor-VIII-containing plasma fraction in a buffer solution containing a sulfated polysaccharide at a pH value approximately in the neutral range;

(b) lowering the pH to a value ranging from 6.0 to 6.4 and adjusting the temperature to between about 0° C. to about 25° C. to precipitate undesired proteins and obtain a Factor-VIII-containing supernatant;

(c) adding at least one member of the group consisting of glycine, sodium chloride and sodium citrate, to said Factor-VIII-containing supernatant to maintain the major part of the immunoglobulins contained in said supernatant in solution;

(d) adding a protein precipitating agent to obtain a Factor-VIII-containing precipitate; and (e) dissolving said Factor-VIII-containing precipatate in a solvent to obtain the final product.

2. A method as set forth in claim 1, wherein said Factor-VIII-containing plasma fraction is a cryoprecipitate.

3. A method as set forth in claim 1, wherein said sulfated polysaccharide is selected from the group consisting of mucopolysaccharide polysulfuric acid ester, pentosan polysulfate and dextran sulfate.

4. A method as set forth in claim 1, wherein the temperature in step (b) is adjusted to about 4° C. to about 8° C.

5. A method as set forth in claim 1, wherein said protein precipitating agent is ethanol.

6. A method as set forth in claim 1, wherein said Factor-VIII-containing precipitate is dissolved in a glycine-citrate-NaCl buffer solution in the presence of an antithrombin III-heparinoid complex or an antithrombin III-heparin complex, and processed into stable form.

7. A method as set forth in claim 1, wherein, upon adding said protein precipitating agent in step (d), a suspension is obtained, which is frozen and re-thawed at a temperature of from about 0° C. to about 4° C., to obtain a supernatant, which is discarded, and a Factor-VIII-containing precipitate, said Factor VIII-containing precipitate is dissolved in a glycine-citrate-NaCl buffer solution in the presence of antithrombin III-heparinoid complex or antitnrombin III-heparin complex, and processed into stable form.

8. A method as set forth in claim 1, wherein albumin is added to the final product for stabilizing purposes.

9. A preparation containing Factor VIII (AHF), having a specific activity of at least 1.5 units of Factor VIII/mg protein, immunoglobulin G (IgG) of from 15 to 30 mg/1000 units of Factor VIII and fibrinogen of from 20 to 40 mg/100 units of Factor VIII produced according to claim 1.

10. A preparation containing Factor VIII (AHF), having a specific activity of at least 1.5 units of Factor VIII/mg protein, immunoglobulin G (IgG) of from 15 to 30 mg/1000 units of Factor VIII and fibrinogen of from 20 to 40 mg/100 units of Factor VIII produced according to claim 8.

* * * * *

UNITED STATES PATENT AND TRADEMARK OFFICE
CERTIFICATE OF CORRECTION

PATENT NO.   :   4,522,751
DATED        :   June 11, 1985
INVENTOR(S)  :   Linnau et al.

It is certified that error appears in the above-identified patent and that said Letters Patent is hereby corrected as shown below:

Column 6, line 44 (Claim 7) "antitnrombin" should read -- antithrombin --.

Signed and Sealed this

Twenty-second Day of October 1985

[SEAL]

Attest:

Attesting Officer

DONALD J. QUIGG

Commissioner of Patents and Trademarks—Designate